United States Patent
Leong et al.

(12) 
(10) Patent No.: US 6,555,061 B1
(45) Date of Patent: Apr. 29, 2003

(54) MULTI-LAYER REAGENT TEST STRIP

(75) Inventors: Koon-wah Leong, Sunnyvale, CA (US); Yeung Siu Yu, Pleasanton, CA (US); Edward Gray Rice, Palo Alto, CA (US)

(73) Assignee: Lifescan, Inc., Milpitas, CA (US)

( * ) Notice: Subject to any disclaimer, the term of this patent is extended or adjusted under 35 U.S.C. 154(b) by 223 days.

(21) Appl. No.: 09/684,716

(22) Filed: Oct. 5, 2000

(51) Int. Cl.[7] .............................................. G01N 33/48
(52) U.S. Cl. ......................... 422/58; 436/169; 436/177; 436/178
(58) Field of Search ................................ 436/169–170, 436/177–178, 95; 422/58, 61

(56) References Cited

U.S. PATENT DOCUMENTS

| | | | |
|---|---|---|---|
| 4,292,272 A | 9/1981 | Kitajima et al. ............... 422/57 |
| 4,631,174 A | 12/1986 | Kondo ......................... 422/56 |
| 4,935,346 A | 6/1990 | Phillips et al. ................. 435/14 |
| 5,200,148 A | 4/1993 | Saito ............................. 422/56 |
| 5,215,712 A | 6/1993 | Kawanishi et al. ............ 422/56 |
| 5,296,192 A | 3/1994 | Carroll et al. ................. 422/56 |
| 5,304,468 A | 4/1994 | Phillips et al. ................. 435/14 |
| 5,310,525 A | 5/1994 | Churchouse et al. .......... 422/56 |
| 5,709,837 A | 1/1998 | Mori et al. .................... 422/56 |
| 5,827,477 A | * 10/1998 | Macho et al. ................. 422/56 |
| 5,968,836 A | 10/1999 | Matzinger et al. ........... 436/169 |
| 6,071,251 A | * 6/2000 | Cunningham et al. ....... 600/584 |

\* cited by examiner

*Primary Examiner*—Lyle A. Alexander

(57) ABSTRACT

A reagent test strip for measuring an analyte concentration in a biological fluid has a spreading mesh sandwiched between a support and a reagent matrix. The support has a through hole that is covered by the mesh. In use, a sample of the fluid is applied through the hole in the support to the spreading mesh. The sample then passes through the mesh to the matrix, which contains a reagent that indicates the analyte concentration by causing a corresponding change in reflectance at its free surface. Optionally, an adhesive layer attaches the mesh, and optionally the matrix as well, to the support.

20 Claims, 1 Drawing Sheet

MULTI-LAYER REAGENT TEST STRIP

BACKGROUND OF THE INVENTION

1. Field of the Invention

This invention relates to a dry test strip for measuring the concentration of an analyte in a biological fluid; more particularly, a test strip that calorimetrically measures the concentration of glucose in whole blood.

2. Description of the Related Art

Many visual test devices have been developed for measuring the concentration of certain analytes in biological fluids. These devices have, for example, measured glucose, cholesterol, proteins, ketones, phenylalanine, or enzymes in blood, urine, or saliva.

Among the devices that are in most widespread use today is the blood glucose monitor. In the U.S. alone, there are estimated to be about 16 million people with diabetes. In order to avoid serious medical problems, such as vision loss, circulatory problems, kidney failure, etc., many of these people monitor their blood glucose on a regular basis and then take the steps necessary to maintain their glucose concentration in an acceptable range.

Reagent strips that are used in these devices contain an indicator that turns a different shade and/or intensity of color, depending on the concentration of glucose in the blood sample that has been applied to the strip. Although some of these strips use reduction chemistries, more commonly they involve an oxidizable dye or dye couple. Some of the strips include an enzyme, such as glucose oxidase, which is capable of oxidizing glucose to gluconic acid and hydrogen peroxide. They also contain an oxidizable dye and a substance having peroxidative activity, which is capable of selectively catalyzing oxidation of the oxidizable dye in the presence of hydrogen peroxide.

U.S. Pat. No. 4,292,272, issued Sep. 29, 1981 to M. Kitajima et al., discloses a multilayer strip for analysis that comprises a light-transmitting support, a reagent layer and a spreading layer, laminated together and to the support. The spreading layer is hydrophilic and supplies a liquid sample applied on its surface at a substantially constant volume per unit area to the reagent layer.

U.S. Pat. No. 4,631,174, issued Dec. 23, 1986 to A. Kondo, discloses a multilayer chemical analysis member that includes, superposed and bonded together, a support, a reagent layer, a porous spreading layer, and a waterproof layer. The waterproof layer has a small opening for applying a drop of sample. The sample diffuses through the spreading layer and into the reagent layer, where a color develops, as discussed above. The purpose of the waterproof layer is to retard evaporation of the sample, which "invariably" spreads outward laterally in the spreading layer, beyond the opening in the waterproof layer. Thereby, the "major portion of fragile spreading layer is protected by the waterproof layer."

U.S. Pat. No. 4,935,346, issued Jun. 19, 1990 to R. Phillips et al., discloses a meter, strip, and method for determining the glucose concentration in a sample of whole blood (see also U.S. Pat. No. 5,304,468). The method involves simply applying a sample of whole blood to a first ("sample") surface of an inert porous matrix that is impregnated with a reagent. The sample migrates toward the opposite, "testing," surface, as the glucose interacts with the reagent to produce a light-absorbing reaction product. A reading of reflectance from the testing surface indicates the glucose concentration. Reflectance measurements are made at two separate wavelengths in order to eliminate interferences. A timing circuit is triggered by an initial decrease in reflectance caused by wetting of the testing surface by the sample having passed through the matrix.

U.S. Pat. No. 5,200,148, issued Apr. 6, 1993 to Y. Saito, discloses a chemical assay tape that includes a support layer and at least one porous spreading layer. A reagent layer (and, optionally, a filter layer) may be sandwiched between the spreading layer and the support or, alternatively, the reagent may be incorporated into the spreading layer. Grooves cut into the spreading layer prevent cracking when the tape is wound.

U.S. Pat. No. 5,215,712, issued Jun. 1, 1993 to T. Kawanishi et al., discloses an apparatus and method for determining ion concentration, specific gravity, or osmotic pressure of a solution. An apparatus of the invention may contain a support having an opening that is covered with a transparent film, which, together with a reagent layer, sandwiches a spreading layer. The support layer is also provided with a retaining part.

U.S. Pat. No. 5,296,192, issued Mar. 22, 1994 to P. Carroll et al., discloses a diagnostic test strip for whole blood that has two support layers, between which are a spreading screen, a separating layer (to remove red blood cells), and a reagent layer.

U.S. Pat. No. 5,310,525, issued May 10, 1994 to S. Churchouse et al., discloses a fluid detection device that includes an impervious container having a fluid entry aperture and contiguous reagent and spreading layers. The device detects an analyte in a fluid that enters the container and spreads within the spreading layer. The analyte then initiates a reaction in the reagent layer to generate a signal.

U.S. Pat. No. 5,709,837, issued on Jan. 20, 1998 to T. Mori et al., discloses a dry analytical element that includes a support, a reagent layer on the support, and a porous spreading layer on the reagent layer. An adhesive layer may be on the regent layer to join the spreading layer.

U.S. Pat. No. 5,968,836, issued on Oct. 19, 1999 to D. Matzinger et al., discloses a reagent strip that has a testing pad sandwiched between a support and a transport medium. A fluid sample is applied to the transport medium and travels through it to the testing pad, in which a reagent reacts with an analyte of interest that is present in the sample to cause a color change. The support has an aperture, through which the color change in the testing pad can be viewed.

A meter that has come into widespread use for self-monitoring of blood glucose is the One Touch® Profile meter, which uses a strip that is described, inter alia, in U.S. Pat. Nos. 4,935,346 and 5,304,468, discussed above. The meter and strip permit a user to measure glucose concentration in a whole blood sample quickly, easily, and accurately. The sample is applied to one surface of the strip and the measurement made on the opposite surface. A portion of the whole blood sample penetrates from the sample surface to the testing surface, and the blood color can be observed from the testing surface.

SUMMARY OF THE INVENTION

The present invention provides a reagent test strip for use in an apparatus for determining an analyte concentration in a sample of biological fluid. The apparatus comprises optical means for detecting intensity of light reflected from a surface of the strip. The strip comprises (a) a support having a through hole for passing a sample of the biological fluid, (b) a mesh, having a first surface adjoining, and covering the hole in, the support, and (c) a reagent matrix adjoining a second surface of the mesh, opposite the first surface, the matrix comprising (i) a sample receiving surface for receiving the sample from the mesh and passing at least a portion of the sample toward a testing surface opposite to the receiving surface and (ii) a reagent for indicating the analyte concentration, by creating at the testing surface a change in reflectance that can be related to the analyte concentration.

One embodiment of a reagent test strip of this invention is used in an apparatus that comprises optical means for detecting intensity of light at wavelengths of about 635 nm and about 700 nm reflected from at least a portion of the testing surface of the strip. In that embodiment, the invention provides a reagent test strip that is suitable for use in a One Touch® Profile whole blood glucose meter (or similar One Touch meter). Since the strip includes a mesh, which spreads the sample laterally, before the sample enters the matrix, it permits a glucose determination to be made using a smaller whole blood sample than is needed for a strip that lacks the mesh.

DETAILED DESCRIPTION OF THE INVENTION

The test strip of the present invention provides a user an opportunity to obtain accurate determinations of analyte concentration, using a smaller sample size than heretofore. When the sample is whole blood, as is the case when the strip is used for self monitoring of blood glucose (SMBG), then the ability to use a smaller sample size is an important advantage.

For brevity and simplicity, the description below will focus on strips for SMBG, but it is clear that the strip of this invention is also suitable for measurements of other analyte concentrations in blood or other sample fluids.

Figure 1:
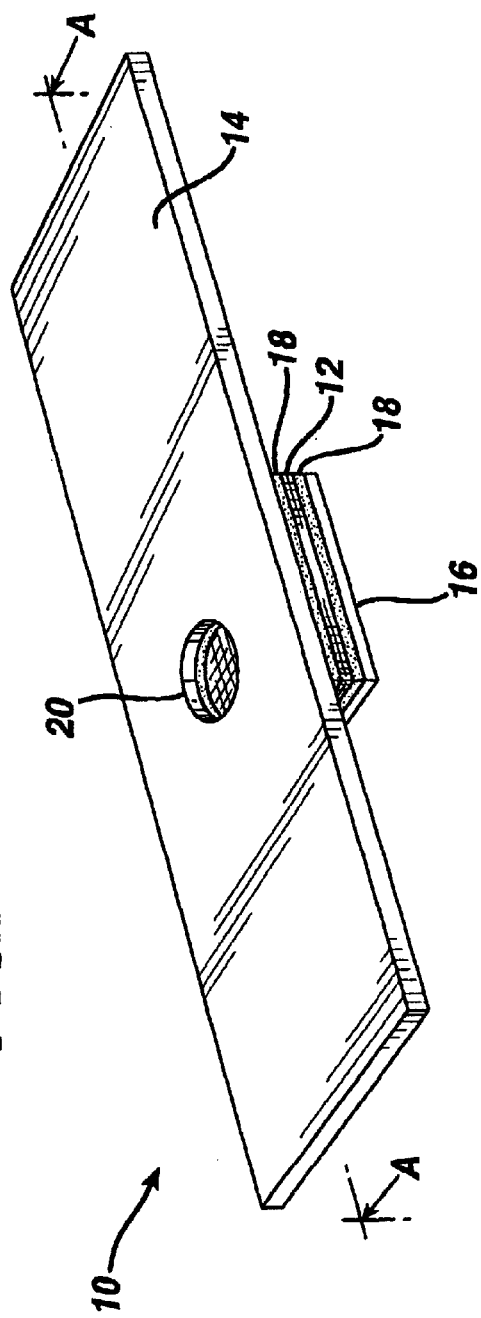
FIG. 1 is a perspective view of an embodiment of a test strip of this invention.
Figure 2:
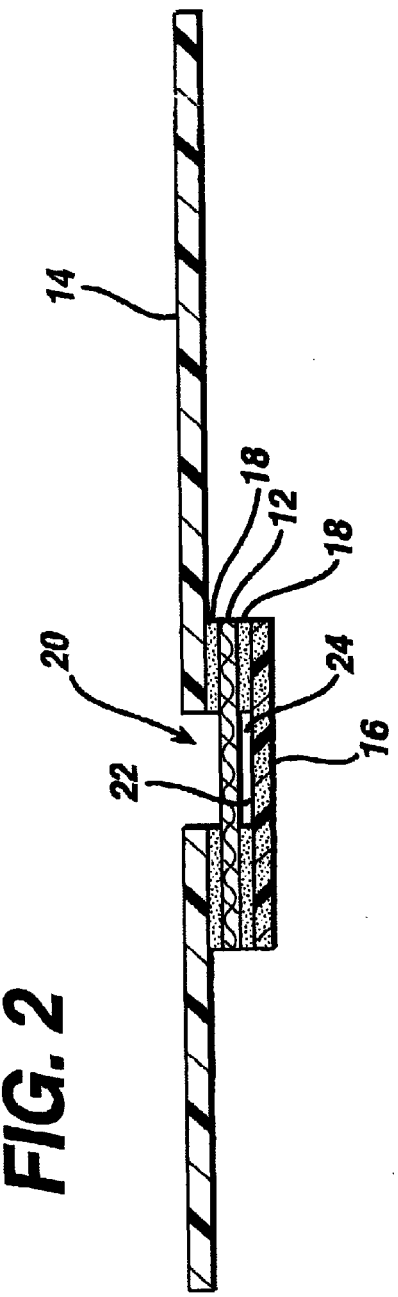
FIG. 2 is a cross section through A—A of the strip of FIG. 1.

FIG. 1 is a perspective view of a strip 10 of the present invention, and FIG. 2 depicts a cross section through A—A. Mesh 12 is sandwiched between support layer 14 and matrix layer 16. Optional adhesive 18 attaches mesh 12 and, optionally, matrix 16 to support 14. Sample inlet 20 is a hole through support layer 14, which is preferably a thermoplastic. In use, a blood sample is applied to mesh 12 through the sample inlet 20. The sample penetrates through mesh 12 spreads out to uniformly cover sample-receiving surface 22 of matrix layer 16. Preferably, the mesh does not appreciably absorb any sample. When adhesive 18 is present, it limits the perimeter of gap 24 and, consequently, the extent to which sample is spread by capillary action.

Preferably, mesh 12 is of a hydrophilic material, woven or non-woven. More preferably, the mesh surface has been modified by, for example, a surfactant coating, plasma treatment, or other well-known process. Polyester or polyamide filament is suitable. Alternatively, the mesh could be of another organic or inorganic material, or metallic, or a combination of more than one of these. The mesh has an open area that is preferably more than 50%. A suitable mesh is available from Sefar America Inc., Depew, N.Y. The mesh is designated as product code RMS 075 and its characteristics are:

material—monofilament polyester
fiber diameter—0.025 mm
mesh thickness—0.05 mm
% open area—75
weave type—square (plain)

The large open area permits the matrix layer to be adhered to the support layer through the mesh, the requirement being that the adhesive layer have a thickness at least about the same as the mesh thickness. The mesh has a surfactant coating that expedites the spread of sample over the matrix layer. The spreading is further enhanced by capillary gap 24 formed between the mesh and matrix layer. The improvement in spreading is particularly pronounced for samples that have high viscosity (e.g., high hematocrit samples).

Since users of the strip may have impaired vision, mesh 12 and the top surface of support 14 (seen in FIG. 1) preferably provide high visual contrast (i.e. if the support surface is light, the mesh is dark, or inversely). More preferably, the mesh is brightly colored or fluorescent in ambient visible illumination, so that the mesh is readily visible in typical ambient lighting. The mesh may be colored by any of a variety of techniques, all of which are well known. Among suitable techniques are using colored filament to prepare the mesh, dying the mesh, etc. It is only the part of the mesh that is visible to the user (typically the front surface) that must be colored to provide this advantage.

Optional adhesive 18 is preferably hydrophobic. A pressure-sensitive adhesive available from 3M, St. Paul, Minn.—product code 415—is an example of a suitable adhesive. Preferably, the adhesive encloses the area over which the sample is to spread. It is convenient, but not essential, to have that area correspond to the area of sample inlet 20. By appropriately choosing the area over which the sample can spread, one can design a strip of this invention to permit a test to be made with a minimum sample volume. If sample inlet 20 is to be coextensive with the area surrounded by adhesive 18, the strip can be made by applying adhesive to support layer 14, then punching a hole into the support and adhesive layers, before laminating mesh 12 and matrix layer 16 to the adhesive-coated support.

The matrix layer is preferably a polyamide membrane that contains a reagent that reacts with glucose in the blood sample to provide a color change that can be related to the glucose concentration in the sample. A suitable reagent comprises glucose oxidase, horseradish peroxidase, and the dye precursor 3-methyl-2 benzothiazolinone hydrazone hydrochloride and 3-dimethylaminobenzoic acid. Additional details concerning suitable membrane and reagent compositions appear in U.S. Pat. No. 5,304,468, issued Apr. 19, 1994, to Phillips et al., incorporated herein by reference.

An anisotropic membrane is also suitable for use as the matrix of the present invention. When such a membrane is used, the larger pores are near the receiving surface and smaller pores near the testing surface. The anisotropic membrane contains a reagent that includes a dye precursor (chromogen) that forms a chromophore indicative of the glucose concentration in the sample. The concentration is determined from the change in reflectance from the testing surface. Red blood cells, which can interfere with the reflectance readings, are trapped in pores near the receiving surface and don't penetrate to the testing surface. A preferred reagent for use with the anisotropic membrane comprises enzymes to produce an oxidizing agent that indicates glucose concentration by oxidizing a dye precursor that is preferably meta [3-methyl 2-benzothiazolinone hydrazone] N-sulfonyl benzenesulfonate monosodium and 8-anilino-1-naphthalene sulfonic acid. Additional details concerning suitable anisotropic membranes and reagent compositions for use with them appear in U.S. Pat. Nos. 5,563,031 and 5,922,530, issued Oct. 8, 1996 and Jul. 13, 1999, respectively, to Y. S. Yu, incorporated herein by reference.

We claim:

1. A reagent test strip for use in an apparatus for measuring an analyte concentration in a biological fluid, comprising
   (a) a support having a top surface, a bottom surface opposite, and a through hole for passing a sample of the biological fluid,
   (b) a mesh, having a first surface adjoining the bottom surface of and covering the hole in, the support, and
   (c) a reagent matrix attached to a second surface of the mesh, opposite the first surface, the matrix comprising
      (i) a sample receiving surface for receiving the sample from the mesh and passing at least a portion of the sample toward a testing surface opposite to the receiving surface and
      (ii) a reagent for indicating the analyte concentration, by creating at the testing surface a change in reflectance that can be related to the analyte concentration; and
   (d) an adhesive layer; and
      wherein the reagent matrix is attached to, and separated from, the second surface of the mesh by the adhesive layer such that a capillary gap is present between the mesh and the reagent matrix.

2. The test strip of claim 1 wherein the reagent is adapted for indicating a glucose concentration in the sample.

3. The test strip of claim 1, in which the support comprises a thermoplastic sheet.

4. The test strip of claim 1, in which the top surface of the support and the mesh provide high visual contrast.

5. The test strip of claim 1, in which the mesh is at least one of brightly colored and fluorescent.

6. The test strip of claim 1, in which the mesh is hydrophilic.

7. The test strip of claim 1, in which the mesh is substantially non-absorbing of the biological fluid.

8. The test strip of claim 1, in which the mesh comprises at least one of polyester filament and polyamide filament.

9. The test strip of claim 1, in which the mesh has an open area that exceeds 50% of the total area of the mesh.

10. The test strip of claim 1, in which the mesh is attached to the support with a pressure-sensitive adhesive.

11. The test strip of claim 10, in which the adhesive is not present where the mesh covers the hole.

12. The test strip of claim 10, in which at least a part of the adhesive extends through the mesh and attaches the reagent matrix to the support.

13. The test strip of claim 10, in which the adhesive is hydrophobic.

14. The test strip of claim 1, in which the reagent matrix comprises a polyamide membrane.

15. The test strip of claim 1, in which the reagent matrix is an anisotropic membrane with larger pores near the sample receiving surface and smaller pores near the testing surface.

16. The test strip of claim 2, in which the reagent comprises a dye precursor that forms a chromophore indicative of the glucose concentration.

17. The test strip of claim 16, in which the dye precursor comprises 3-methyl-2-benzothiazolinone hydrazone hydrochloride and dimethylaminobenzoic acid.

18. The test strip of claim 16, in which the dye precursor comprises meta [3-methyl 2-benzothiazolinone hydrazone] N-sulfonyl benzenesulfonate monosodium and 8-anilino-1-naphthalene sulfonic acid.

19. The test strip of claim 17, in which the reagent matrix comprises a polyamide membrane.

20. The test strip of claim 18, in which he reagent matrix comprises an anisotropic membrane with larger pores near the receiving surface and smaller pores near the testing surface.

* * * * *